US010332699B2

(12) United States Patent
Radmer et al.

(10) Patent No.: US 10,332,699 B2
(45) Date of Patent: Jun. 25, 2019

(54) POWER EFFICIENT ADD-ON DEVICE

(71) Applicant: Novo Nordisk A/S, Bagsvaerd (DK)

(72) Inventors: Bo Radmer, Hilleroed (DK); Sara Niemann, Vanloese (DK); Nikolai Byskov, Noerrebro (DK); Carsten Soerensen, Frederiksberg (DK); Michael Ejstrup Hansen, Morud (DK); Roger Harrington, Skaevinge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/763,888

(22) PCT Filed: Sep. 29, 2016

(86) PCT No.: PCT/EP2016/073289
§ 371 (c)(1),
(2) Date: Mar. 28, 2018

(87) PCT Pub. No.: WO2017/055468
PCT Pub. Date: Apr. 6, 2017

(65) Prior Publication Data
US 2018/0272072 A1  Sep. 27, 2018

(30) Foreign Application Priority Data

Sep. 30, 2015 (EP) .................................... 15187764

(51) Int. Cl.
*A61M 5/20* (2006.01)
*H01H 9/54* (2006.01)
(Continued)

(52) U.S. Cl.
CPC ............ *H01H 9/54* (2013.01); *A61M 5/2033* (2013.01); *A61M 5/2422* (2013.01);
(Continued)

(58) Field of Classification Search
CPC ..... H01H 9/54; A61M 5/2033; A61M 5/2422; A61M 5/3155; A61M 5/3202;
(Continued)

(56) References Cited

U.S. PATENT DOCUMENTS 8,743,662 B2  6/2014  Sjolund et al.
8,817,258 B2  8/2014  Whalley et al.
(Continued)

FOREIGN PATENT DOCUMENTS

EP  1354609 A2  10/2003
WO  9730742  8/1997
(Continued)

*Primary Examiner* — Daniel J Cavallari
(74) *Attorney, Agent, or Firm* — Wesley Nicolas

(57) ABSTRACT

An electronically controlled add-on device with a switch arrangement comprises a powered switch which is open during most of its lifetime, i.e. during both storage and operational use. More specifically, in one embodiment the add-on device comprises a secondary switch so that there are an open and a closed switch. The logics of the electronic circuitry control the circuitry so that the closed switch will be un-powered and the open switch will be powered. When the switch is mechanically changed, both switches are changed by the controller so that the closed switch will be un-powered and the open switch will be powered.

15 Claims, 7 Drawing Sheets

(51) Int. Cl.
*A61M 5/32* (2006.01)
*A61M 5/24* (2006.01)
*A61M 5/315* (2006.01)
*A61M 5/31* (2006.01)

(52) U.S. Cl.
CPC ........ *A61M 5/3155* (2013.01); *A61M 5/3202* (2013.01); *A61M 5/3213* (2013.01); *A61M 5/20* (2013.01); *A61M 5/24* (2013.01); *A61M 2005/3126* (2013.01); *A61M 2205/14* (2013.01); *A61M 2205/50* (2013.01); *A61M 2205/8206* (2013.01); *A61M 2205/8212* (2013.01)

(58) Field of Classification Search
CPC ............ A61M 5/3213; A61M 2205/14; A61M 2205/50; A61M 2005/3126; A61M 5/24; A61M 5/20; A61M 2205/8206; A61M 2205/8212

See application file for complete search history.

(56) References Cited

U.S. PATENT DOCUMENTS

2011/0295215 A1 12/2011 Nielsen et al.
2012/0252279 A1 10/2012 Lee et al.

FOREIGN PATENT DOCUMENTS

| WO | 2012152628 | A1 | 11/2012 | | |
| WO | 2013004844 | A1 | 1/2013 | | |
| WO | WO-2014020010 | A3 * | 5/2014 | .............. | A61M 5/24 |
| WO | 2014161952 | A1 | 10/2014 | | |

* cited by examiner

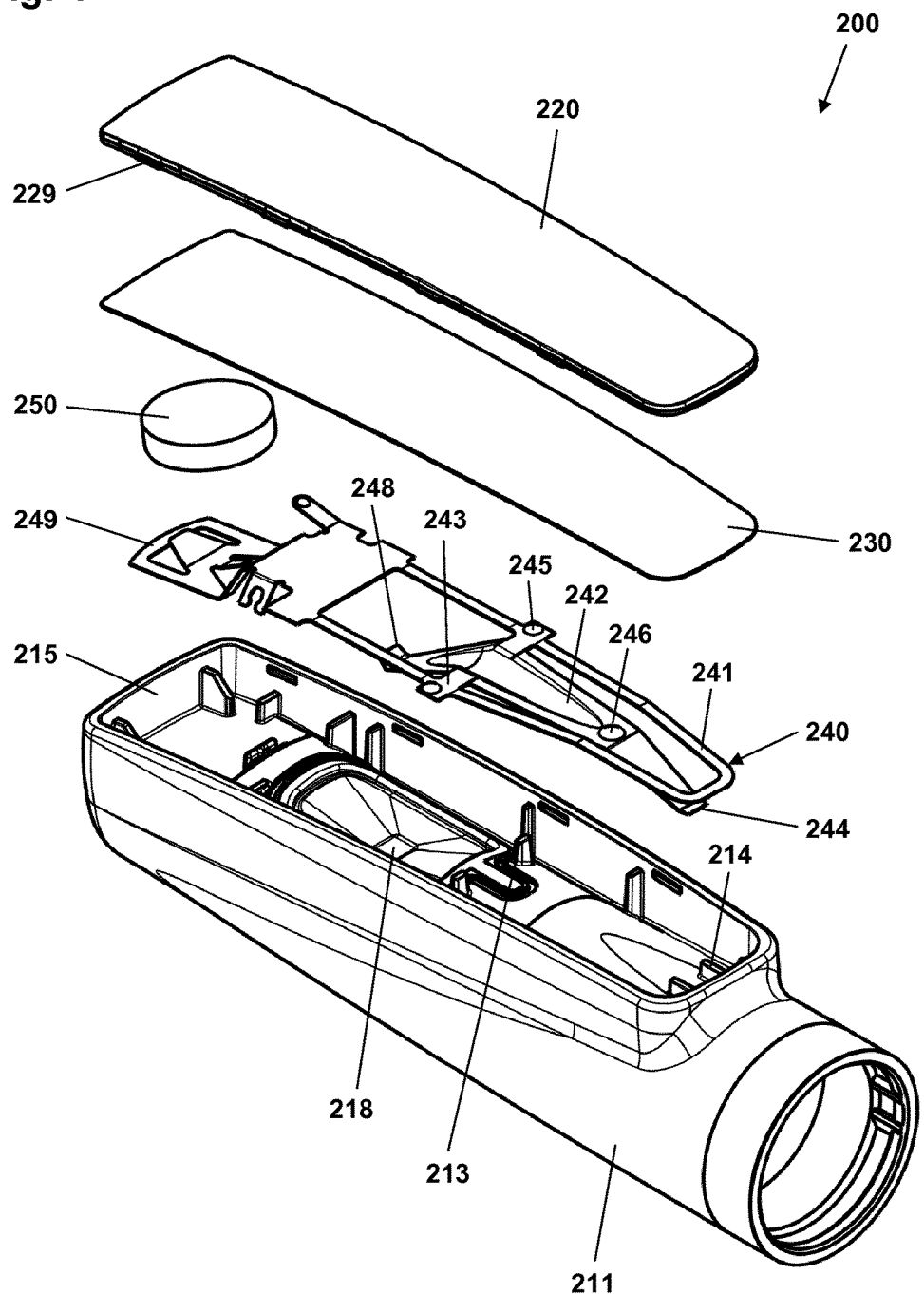

POWER EFFICIENT ADD-ON DEVICE

CROSS-REFERENCE TO RELATED APPLICATIONS

This application is a 35 U.S.C. § 371 National Stage application of International Application PCT/EP2016/073289 (published as WO 2017/055468), filed Sep. 29, 2016, which claims priority to European Patent Application 15187764.4, filed Sep. 30, 2015, the contents thereof which are incorporated by reference in their entirety.

The present invention generally relates to a battery-powered add-on device to be used in combination with a receiving device, e.g. a medical device. In a specific aspect the device is in the form of an add-on device to be used in combination with a drug delivery device, e.g. in the form of a cap to be used in combination with a pen-type drug delivery device or an inhalation device.

BACKGROUND OF THE INVENTION

In the disclosure of the present invention reference is mostly made to drug delivery devices, such devices being used e.g. in the treatment of diabetes, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

The typical diabetes patient will require injections of insulin several times during the course of a week or a day. For other types of drug the intervals between drug deliveries may be shorter or longer. However, typical injection devices do not address the problem of a user not remembering when the last injection was administered.

Even shortly after administering a dose of insulin, the user now and then will be in doubt as to whether he actually carried out an injection or not. This could be after minutes or even hours after the intended time for performing an administration. Thus, there exist the potential hazard that the patient chooses not to take his or her medication or that it is taken twice.

Some prior art devices, such as the electronic drug delivery device disclosed in WO 97/30742, are provided with an electronic monitoring system adapted to automatically start an electronic timer when a selected dose is expelled and to show the progress in time on an electronic display. Such an injection device generally provides a satisfactorily solution to the problem addressed above. However, for simpler devices such as disposable drug delivery devices, i.e. so-called pre-filled devices, the incorporation of this kind of electronics would normally not be economically viable. In addition, such a solution may not be environmentally acceptable due to the potential increase in the disposal of electronic components.

Addressing this issue, U.S. Pat. No. 8,743,662 discloses a cap-formed electronic timer device which is intended to be used with pre-filled drug delivery devices of the pen-type to replace the standard cap. The cap comprises a switch mechanism adapted to detect when the cap is placed on the delivery device, and released when the cap is removed from the dosing device, the engagement and/or releasing of the switch mechanism causing the timer unit to reset (preferably with a delay of some seconds), the time since the timer unit was last reset thereby indicating the time that has elapsed since the cap was removed, this again indicating when the drug delivery likely was used to deliver a dose of drug. This functionality is often termed "time-since-last-dose". The cap is provided with a non-replaceable power source, e.g. a button cell.

Using the same form factor U.S. Pat. No. 8,817,258 discloses a cap-device which is adapted to measure the amount of drug remaining in the cartridge and thereby to create a log of dose amounts expelled from the cartridge between two measurements. Addressing the issue of detecting the size of an expelled amount of drug WO 2014/161952 discloses a ring-formed add-on device adapted to be mounted on the body portion of a drug delivery device, the device being turned on and off when the cap is removed and reattached.

A cap-formed electronic add-on device to be used in combination with a handheld drug delivery device has also been proposed in the form of a blood glucose meter (BGM), see e.g. WO 2012/152628.

To register use of the pen device, the add-on device may be provided with a powered switch which needs to change state to detect a cap-on/cap-off event. For example, to prevent power consumption after manufacturing and during storage prior to use when the cap is mounted on a pen device for the first time (shelf life), the powered switch may be open during storage. However, this means that the switch is open during use of the pen device and closed between uses of the device. As the latter state represents most of the use time for the add-on device this is power-costly. Alternatively, a powered switch may be closed when it is off the pen and open when it is mounted on the pen, however, this would be power-costly during storage. In the present context a powered switch defines a switch in which an electric potential is applied across the switch, this allowing a current to flow when the switch is in a closed state and prevents (apart from any leak current) a current to flow when the switch is in an open state.

EP 1 354 609 discloses a jet injector device having a suction pump which can enter a low-power sleeping mode to save energy.

Having regard to the above, it is an object of the present invention to provide an electronic add-on device to be used in combination with a receiving device, and which is both user-friendly and power-efficient during its entire life-time, such an arrangement being relevant for any electronic device having a use-scenario of the type described above. It is a further object to provide such a device in the form of a cap-device to be used in combination with a drug delivery device and which at least in part is controlled when the cap is removed and reattached to the device.

DISCLOSURE OF THE INVENTION

In the disclosure of the present invention, embodiments and aspects will be described which will address one or more of the above objects or which will address objects apparent from the below disclosure as well as from the description of exemplary embodiments.

According to a general aspect of the invention, the above problem is addressed by providing an electronically controlled add-on device with a switch arrangement comprising a powered switch which is open during most of its lifetime, i.e. during both storage and operational use.

This can be achieved by the introduction of a secondary switch so that there are an open and a closed switch. The logics of the electronic circuitry may then control the circuitry so that the closed switch will be un-powered and the open switch will be powered. When the switch is mechanically changed (at cap-off or cap-on), both switches are changed by the controller so that the closed switch will be un-powered and the open switch will be powered.

Thus, according to a general aspect of the invention, an electronic add-on device adapted to be mounted on a receiving device comprises electronic circuitry, a power source, and a switch arrangement having a mounted state and an un-mounted state. The switch arrangement is configured to have an open and powered switch in both states, with the electronic circuitry being arranged to detect a change of state, from mounted to un-mounted and/or from un-mounted to mounted by detecting closure of at least one powered switch. In other words the switch arrangement of the present invention is adapted to automatically toggle between two low-power states, this in contrast to prior art arrangements having only a single automated sleep mode.

Alternatively a transition switch may be used which is always powered. In this concept a current is only running through the switch in the very limited time when the moved switch member touches the powered conductive area when moving from one position to another.

In this way a switch set-up is provided which is both power-efficient and user friendly, this in contrast to a traditional solution in which the user has to manipulate the device to manually switch it between a storage and an in-use operational state, e.g. by pulling a tap blocking current flow.

Each switch may comprise a stationary switch point arranged on a stationary portion of the add-on device and a moving switch point arranged on a moving portion thereof. In exemplary embodiments the power state of the stationary switch point is controlled by the electronic circuitry.

Thus, in a first specific aspect of the invention an add-on device adapted to be mounted on a receiving device is provided, the add-on device comprising electronic circuitry, a power source and a switch arrangement comprising a first switch and a second switch. The switch arrangement has a first state in which the first switch is open and powered, and the second switch is closed and un-powered. The switch arrangement has an intermediate state in which the first switch is closed and powered, and the second switch is closed and powered. The switch arrangement has a second state in which the first switch is closed and un-powered, and the second switch is open and powered. The electronic circuitry is arranged to detect, with the switch arrangement in the first state, when the first switch is closed, and subsequently change the state of the second switch from un-powered to powered, thereby shifting the switch arrangement to the intermediate state, and the electronic circuitry is arranged to detect, with the switch arrangement in the intermediate state, when the second switch is opened, and subsequently change the state of the first switch from powered to un-powered, thereby shifting the switch arrangement to the second state. By this arrangement an add-on device is provided which can be stored in the first "off" state as well as being mounted on a receiving device corresponding to the second "on" state, both states being characterized by having a low power consumption due to a powered open switch. When the switch arrangement is used in a cap device adapted to be mounted on a drug delivery device the created switch pattern can be used to detect a "cap-on" event (i.e. the cap is put on).

The electronic circuitry may further be arranged to detect, with the switch arrangement in the second state, when the second switch is closed, and subsequently change the state of the first switch from un-powered to powered, thereby shifting the switch arrangement to the intermediate state, and to detect, with the switch arrangement in the intermediate state, when the first switch is opened, and subsequently change the state of the second switch from powered to un-powered, thereby shifting the switch arrangement to the first state. When the switch arrangement is used in a cap device adapted to be mounted on a drug delivery device the created switch pattern can be used to detect a "cap-off" event (i.e. the cap is taken off).

In an exemplary embodiment the electronic add-on device comprises a stationary portion and a moving portion, wherein the first switch comprises a first stationary switch point arranged on the stationary portion and a first moving switch point arranged on the moving portion, the second switch comprises a second stationary switch point arranged on the stationary portion and a second moving switch point arranged on the moving portion, and the moving portion can be actuated from a first state through an intermediate to a second state corresponding to the switch arrangement first, intermediate and second states.

In a second specific aspect of the invention an add-on device adapted to be mounted on a receiving device is provided, the add-on device comprising electronic circuitry, a power source, and a switch arrangement comprising a first switch and a second switch. The switch arrangement has a first state in which the first switch is open and powered, and the second switch is closed and un-powered. The switch arrangement has a first intermediate state in which the first switch is open and powered, and the second switch is open and un-powered. The switch arrangement has a second state in which the first switch is closed and un-powered, and the second switch is open and powered. The electronic circuitry is arranged to detect, with the switch arrangement in the first intermediate state, when the first switch is closed, and subsequently change the state of the first switch from powered to un-powered and the state of the second switch from un-powered to powered, thereby shifting the switch arrangement to the second state.

By this arrangement an add-on device is provided which can be stored in the first "off" state as well as being mounted on a receiving device corresponding to the second "on" state, both states being characterized by having a low power consumption due to a powered open switch. When the switch arrangement is used in a cap device adapted to be mounted on a drug delivery device the created switch pattern can be used to detect a "cap-on" event (i.e. the cap is put on).

The switch arrangement may further have a second intermediate state in which the first switch is open and un-powered, and the second switch is open and powered, the electronic circuitry being arranged to detect, with the switch arrangement in the second intermediate state, when the second switch is closed, and subsequently change the state of the first switch from un-powered to powered and the state of the second switch from powered to un-powered, thereby shifting the switch arrangement to the first state. When the switch arrangement is used in a cap device adapted to be mounted on a drug delivery device the created switch pattern can be used to detect a "cap-off" event (i.e. the cap is taken off).

In an exemplary embodiment the electronic add-on device comprises a stationary portion and a moving portion, wherein the first switch comprises a first stationary switch point arranged on the stationary portion and a common moving switch point arranged on the moving portion, the second switch comprises a second stationary switch point arranged on the stationary portion and the common moving switch point arranged on the moving portion, and the moving portion can be actuated from a first state through an intermediate to a second state corresponding to the switch arrangement first, intermediate and second states.

In a third specific aspect of the invention an add-on device adapted to be mounted on a receiving device is provided, the add-on device comprising electronic circuitry, a power source, and a switch arrangement comprising a powered switch. The switch comprises a stationary switch point arranged on the stationary portion and a moving switch point arranged on the moving portion. The switch arrangement has a first state in which the moving switch point is in a first position and the switch is open. The switch arrangement has an intermediate state in which the switch points are in contact and the switch thus closed. The switch arrangement has a second state in which the moving switch point is in a second position and the switch is open. The electronic circuitry is arranged to detect a transition event when the switch is closed and subsequently opened.

The electronic add-on device may be mounted on the receiving device from an off-position through an intermediate position to an on-position corresponding to the switch arrangement first, intermediate and second states, and it may be removed from the receiving device from an on-position through an intermediate position to an off-position corresponding to the switch arrangement second, intermediate and first states.

In the above-described electronic add-on devices the electronic circuitry is adapted to create a time-stamp when a powered switch is closed or opened. A number of time-stamps may be used to create a log of events, e.g. cap-off events. The add-on device may comprise a display controlled to display (i) a time parameter indicating the time when a given event was detected, e.g. using the HH:MM format, or (ii) a time parameter indicating the time since the event, e.g. a dynamic timer using the HH:MM format or a simple version using segments for e.g. each hour.

In a further aspect of the invention an assembly is provided comprising an add-on device as described above in combination with a receiving device, the receiving device being in the form of a drug delivery device, and the add-on device being in the form of a cap adapted to be mounted on the drug delivery device.

The drug delivery device may comprise or be adapted to receive a drug-filled cartridge. The device may comprise an expelling assembly comprising a piston rod adapted to engage and axially displace a piston in a loaded cartridge in a distal direction to thereby expel a dose of drug from the cartridge, dose setting means allowing a user to set a dose amount to be expelled by rotation of a dose setting member, and means adapted to expel the set dose amount.

Alternatively, the drug delivery device may comprise a drive member, a drive spring coupled to the drive member, dose setting means allowing a user to simultaneously set a dose amount to be expelled and strain the drive spring correspondingly by rotation of the drive member, and release means adapted to release the strained drive spring to rotate the drive member to expel the set dose amount.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof.

BRIEF DESCRIPTION OF THE DRAWINGS

In the following exemplary embodiments of the invention will be described with reference to the drawings, wherein
FIG. 4 shows in exploded view the cap device of FIG. 2,
FIGS. 5A-5E show in a schematic representation a first embodiment of a switch arrangement in different operational states.

In the figures like structures are mainly identified by like reference numerals.

DESCRIPTION OF EXEMPLARY EMBODIMENTS

Figure 1A:
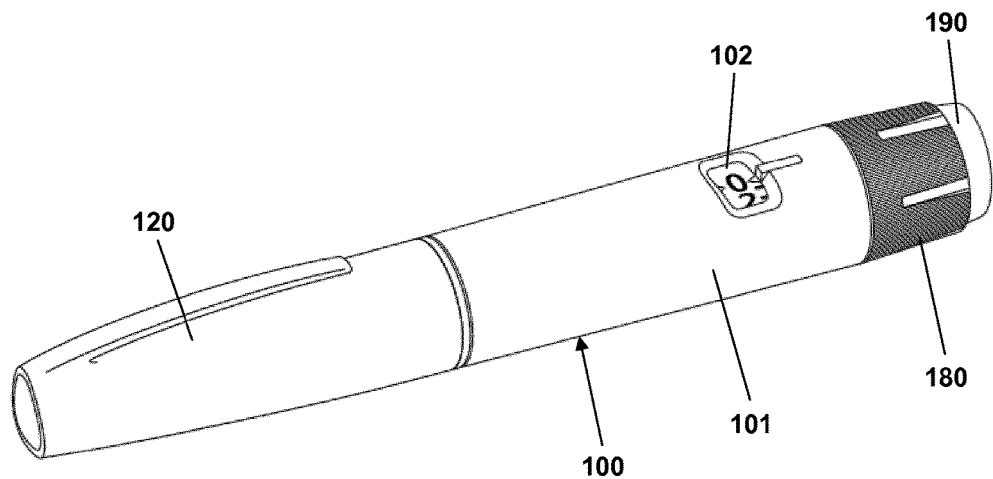
FIG. 1A shows a pen-formed drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessary can be assembled to provide a unitary or functional assembly during a given assembly procedure but is merely used to describe components grouped together as being functionally more closely related.

Before turning to embodiments of the present invention per se, an example of a pre-filled drug delivery will be described, the device representing an example of a receiving device with which embodiments of the present invention is intended to be used in combination with. Although the pen-formed drug delivery device 100 shown in FIG. 1 may represent a "generic" drug delivery device, the actually shown device is a FlexTouch® pre-filled drug delivery pen as manufactured and sold by Novo Nordisk A/S, Bagsværd, Denmark.

The pen device 100 comprises a cap part 120 and a main part having a proximal body or drive assembly portion with a housing 101 in which a drug expelling mechanism is arranged or integrated, and a distal cartridge holder portion 110 in which a drug-filled transparent cartridge 130 with a distal needle-penetrable septum is arranged and retained in place by a non-removable cartridge holder attached to the proximal portion, the cartridge holder having openings allowing a portion of the cartridge to be inspected as well as distal coupling means 115 allowing a needle assembly to be releasably mounted. The cartridge is provided with a piston driven by a piston rod forming part of the expelling mechanism and may for example contain an insulin, GLP-1 or growth hormone formulation. The mechanism comprises a scale drum member provided with a plurality of dose size indices, the scale drum member being arranged rotationally corresponding to the general axis. The housing comprises a display opening (or window) 102 arranged to show a scale drum member dose size indicia corresponding to a set dose. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
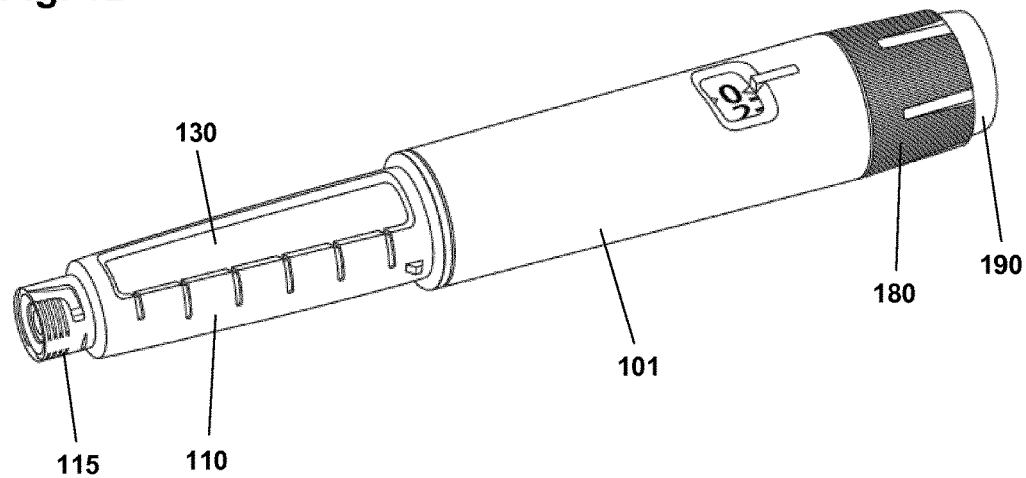
FIG. 1B shows the pen device of FIG. 1A with the pen cap removed.

Although FIGS. 1A and 1B show a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

Figure 2:
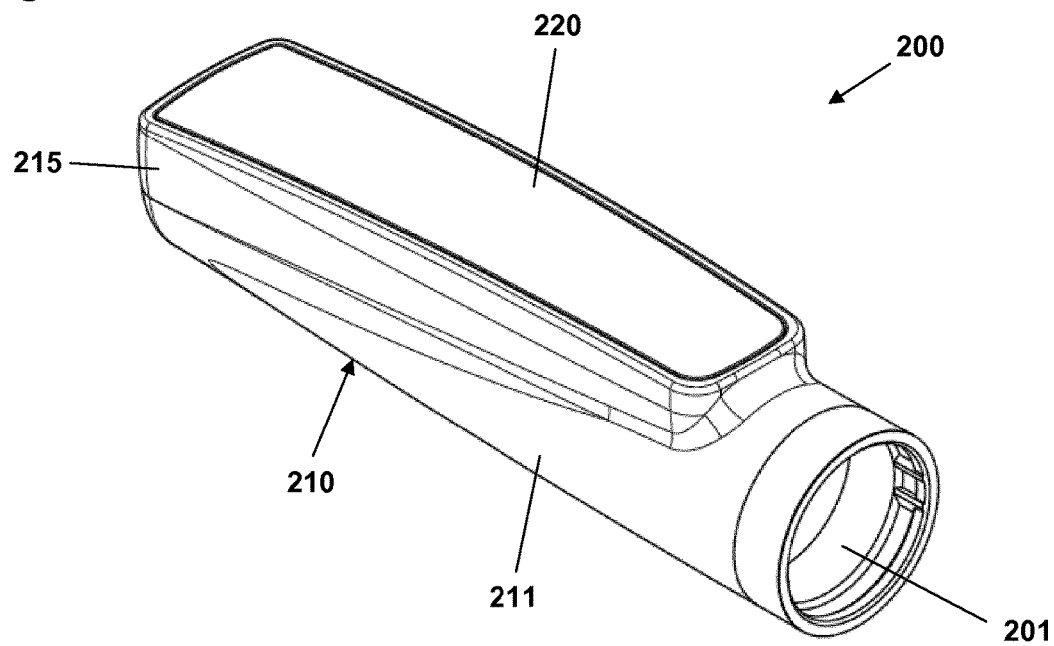
FIG. 2 shows an embodiment of an add-on cap device.

FIG. 2 shows an electronic add-on device in the form of a cap device adapted to replace the standard cap 120 shown in FIG. 1A. The cap device 200 comprises a housing 210 having a generally cylindrical housing portion 211 forming an inner cavity 201 adapted to receive the cartridge holder portion of a corresponding pen device, as well as an outer radially extending wall portion 215 onto which a cover member 220 is mounted, this forming an outer compartment between the cylindrical housing portion and the cover member, the compartment being adapted to accommodate the electronic circuitry and associated components providing the functionality of the electronic add-on device.

Figure 3:
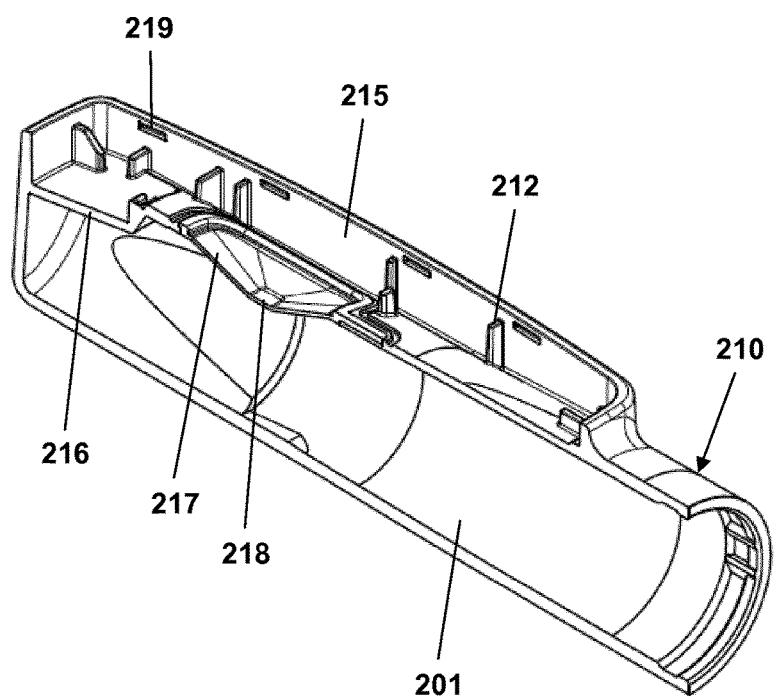
FIG. 3 shows in cross-sectional view a cap device housing.

FIG. 3 shows a cross-sectional view of the cap housing 210 shown in FIG. 2. In order to protect the electronic circuitry from being contaminated with fluid drugs from the cartridge, e.g. due to a mounted needle, the compartment is sealed towards the inner cavity by a partition wall portion 216 having no openings. In order to detect that the cap is mounted on and removed from the pen device a switch is provided. The switch may be based on e.g. optical, magnetic or mechanical detection of the presence of a cartridge holder portion being inserted into the cap cavity. In the shown embodiment the cap device comprises a mechanical switch assembly arranged in the sealed compartment, the mechanical movement of the cartridge holder portion being transferred to the switch via a flexible dome portion 217 of the partition wall 216. In the shown embodiment the flexible portion is provided by a rubber-like 217 insert integrally formed by 2K moulding. The flexible dome has a central portion 218 protruding slightly into the cavity and is adapted to engage the cartridge holder portion.

The cap housing is further provided with a number of supports 212 for the electronic circuitry, e.g. switch member and printed circuit board (PCB), as well as a number of snap cavities 219 for corresponding protrusions 229 on the cover member 220.

FIG. 4 shows the main components of the cap device 200. In addition to the above-described housing 210 and cover member 220, the cap device comprises a flexible PCB 230 with mounted electronic components (not shown), a flexible switch member 240 and a power source in the form of a button cell 250.

The switch member 240 is formed from a metal sheet and comprises a frame portion 241 and a central strip portion 242 connected to the frame portion by a pair of bridge portions 243 supported by supports 213, this allowing the two portions to move relatively to each other. The strip portion comprises a distal free 248 end adapted to be seated in the dome central portion 218 and thereby to be actuated when the cap device 200 is mounted on a pen, and a proximal free 244 end in supported sliding engagement with cap housing 216 between protrusions 214. The switch member is provided with a pair of first moving switch points 245 arranged on the frame portion and a second moving switch point 246 arranged on the strip portion. The pair of first switch points provides redundancy. The switch member also comprises a portion 249 engaging the button cell 250. The functionality of the switch member 240 will be described in greater detail below with reference to FIGS. 5A-5E.

The flexible PCB 230 comprises the electronic circuitry, e.g. processor, memory, display controller, as well as on its lower surface first stationary switch points adapted to engage the first moving switch points 245, and a second stationary switch point adapted to engage the second moving switch point 246. If the cap device is provided with display means, this may be in the form of an LCD or a number of LEDs mounted on the PCB. Alternatively a display may be formed integrally with the cover member, e.g. a flexible LCD laminated to the cover member. As a further alternative, display means may be provided by a printed display formed, for example, directly on the flexible PCB. As a yet further alternative the cap device may comprise no display but be provided with communication means allowing data to be transferred to an external device for displaying, e.g. a smartphone.

The shown embodiment provides a relatively simple functionality in the form of indicating time-since-last-dose based on registering when the cap has been removed for a predetermined amount of time. The time-since-last-dose may be shown using a simple segment display, e.g. four segments each representing an hour, or a display capable of showing a period in e.g. hours and minutes. The cap may also be provided with a reminder functionality based on reminders stored in the memory. The reminders may be set using an external device and be communicated wirelessly to the cap device.

In alternative embodiments the add-on cap device may be provided with sensor means adapted to measure the amount of drug remaining in the cartridge and thereby to create a log of dose amounts expelled from the cartridge between two measurements. Further, a blood glucose meter (BGM) may also be incorporated in the cap device.

Having described an exemplary embodiment of a cap-formed add-on device adapted to be used in combination with a standard pen-formed drug delivery device, a number of power-efficient switch arrangements suitable for use in such a device or any other add-on device for which the issue of power consumption during both shelf life and subsequent in-use life is relevant will be described.

With reference to FIGS. 5A-5E a first embodiment of a switch arrangement 300 will be described, the figures showing a schematic representation of the switch arrangement in different operational states. As indicated above, the first embodiment corresponds to the switch arrangement incorporated in the cap device of FIGS. 2-4. The switch arrangement comprises a stationary portion 330 (e.g. a PCB) and a moving portion 340. The moving portion is in the form of a strip-formed flexible metal member held in place relative to the stationary part by supporting structures 313, 316 formed by a further supporting structure. The strip member comprises a free end portion 348 adapted to engage directly or indirectly a given structure to which the switch arrangement is being attached, the strip member being allowed to move and flex slightly. The switch arrangement further comprises electronic circuitry and a power source (not shown). The holding structure 313 is only shown in FIGS. 5A and 5E.

The switch arrangement comprises a first switch comprising a first stationary switch point 335 arranged on the stationary portion and a first moving switch point 345 arranged on the moving portion, and a second switch comprising a second stationary switch point 336 arranged on the stationary portion and a second moving switch point 346 arranged on the moving portion. The switch points are connected to and controlled by the electronic circuitry whereby a voltage difference can be established between a pair of contact points and thereby a powered switch provided, this allowing the electronic circuitry to detect when a given powered switch is closed or opened.

Figure 5A:
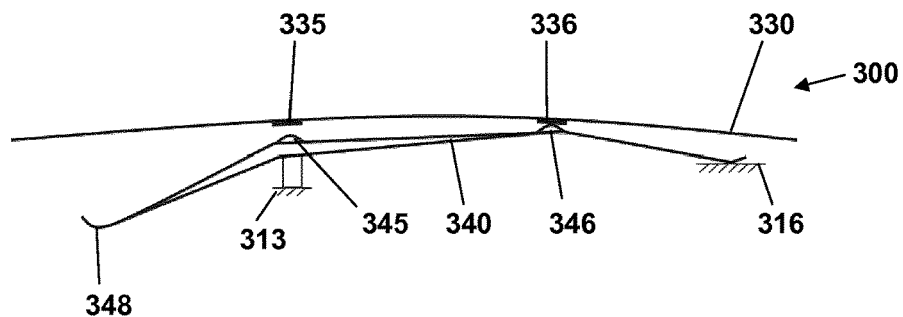

Turning to FIG. 5A the switch arrangement is shown in a first state in which the first switch 335, 345 is open and powered, and the second switch 336, 346 is closed and un-powered.

Figure 5B:
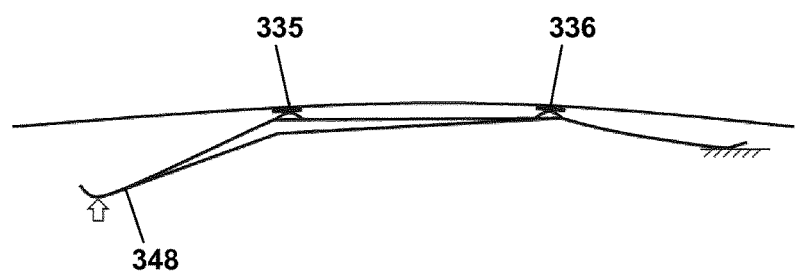

FIG. 5B shows the switch arrangement in an intermediate state in which the strip free end 348 has been moved upwards whereby the first switch has been closed but is still powered. The second switch is still closed but is now powered, this being controlled by the electronic circuitry which is arranged to detect, with the switch arrangement in the first state, when the first switch is closed, and subsequently change the state of the second switch from un-powered to powered.

Figure 5C:
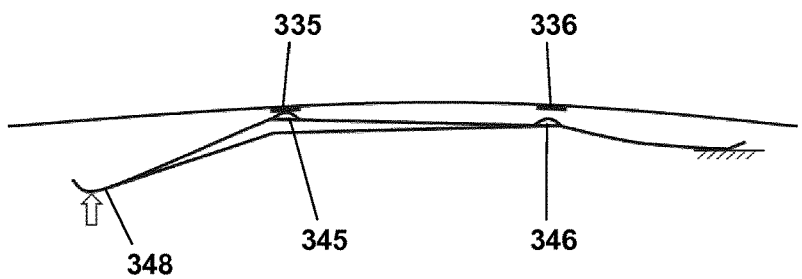

FIG. 5C shows the switch arrangement in a second state in which the strip free end 348 has been moved further upwards whereby the second switch has been opened as the strip pivots but is still powered. The first switch is still closed but is now un-powered, this being controlled by the electronic circuitry which is arranged to detect, with the switch arrangement in the intermediate state, when the second switch is opened, and subsequently change the state of the first switch from powered to un-powered.

As appears, a cap-formed add-on device provided with the above-described switch arrangement can be stored in the first state (cap-off) as well as being mounted on a pen device (cap-on) corresponding to the second state, both states being characterized by having a low power consumption due to a powered open switch. When the add-on cap is mounted on the receiving pen device the switches will change state as follows ("1"=open, "0"=closed):

|  | Switch 1 | Switch 2 |
| --- | --- | --- |
| 1$^{st}$ state | 1 | 0 |
| Interm. state | 0 | 0 |
| 2$^{nd}$ state | 0 | 1 |

The above switch pattern can then be detected as a "cap-on" event (i.e. the cap is put on).

Figure 5D:
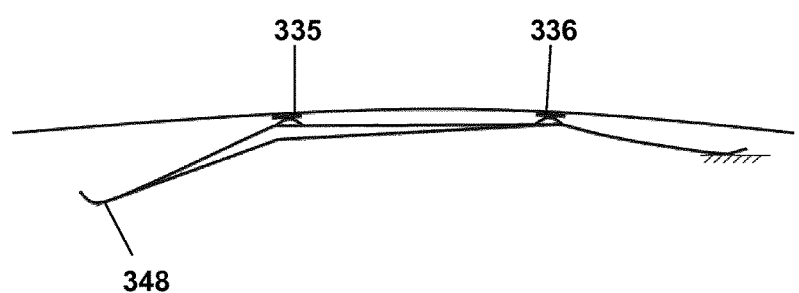

FIG. 5D shows the switch arrangement back in the intermediate state in which the strip free end 348 has been moved downwards whereby the second switch has been closed but is still powered. The first switch is still closed but is now powered, this being controlled by the electronic circuitry which is arranged to detect, with the switch arrangement in the second state, when the second switch is closed, and subsequently change the state of the first switch from un-powered to powered.

Figure 5E:
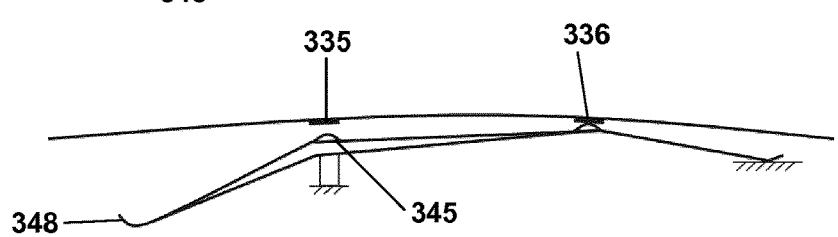

FIG. 5E shows the switch arrangement back in the first state in which the strip free end 348 has been moved further downwards whereby the first switch has been opened as the strip pivots but is still powered. The second switch is still closed but is now un-powered, this being controlled by the electronic circuitry which is arranged to detect, with the switch arrangement in the intermediate state, when the first switch is opened, and subsequently change the state of the second switch from powered to un-powered.

As appears, when the cap-formed add-on device is removed from the pen device it will return to the low-power cap-off state corresponding to the first state. When the add-on cap is removed from the receiving pen device the switches will change state as follows:

|  | Switch 1 | Switch 2 |
| --- | --- | --- |
| 2$^{nd}$ state | 0 | 1 |
| Interm. state | 0 | 0 |
| 1$^{st}$ state | 1 | 0 |

The above switch pattern can then be detected as a "cap-off" event (i.e. the cap is taken off).

In addition to having two low-power states and the ability to positively detect both cap-on and cap-off events, the above-described switch arrangement also allows a switch defect to be detected in case the transitional intermediate state with two closed and powered switches is not detected.

With reference to FIGS. 6A-6E a second embodiment of a switch arrangement 400 will be described, the figures showing a schematic representation of the switch arrangement in different operational states. The switch arrangement comprises a stationary portion 430 (e.g. a PCB) and a moving portion 440. The moving portion is in the form of a strip-formed flexible metal member held in place relative to the stationary part by a holding structure 410 formed by a stationary part. The strip member comprises a contact portion 448 adapted to engage a given structure to which the switch arrangement is being attached. When the contact portion is moved upwards the free end 447 of the strip member is moved in sliding engagement with the stationary portion. The switch arrangement further comprises electronic circuitry and a power source (not shown).

The switch arrangement comprises a first switch comprising a first stationary switch point 435 arranged on the stationary portion and a common moving switch point 445 arranged on the moving portion in the vicinity of the free end 447, and a second switch comprising a second stationary switch point 436 arranged on the stationary portion and the common moving switch point 445 arranged on the moving portion. The switch points are connected to and controlled by the electronic circuitry whereby a voltage difference can be established between a pair of contact points and thereby a powered switch provided, this allowing the electronic circuitry to detect when a given powered switch is closed or opened.

Figure 6A:
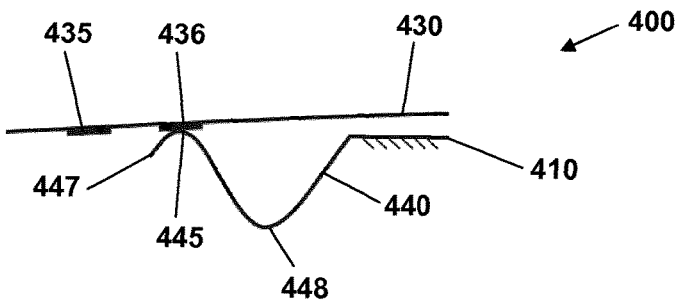
FIGS. 6A-6E show in a schematic representation a second embodiment of a switch arrangement in different operational states.

Turning to FIG. 6A the switch arrangement is shown in a first state in which the first switch 435, 445 is open and powered, and the second switch 436, 445 is closed and un-powered.

Figure 6B:
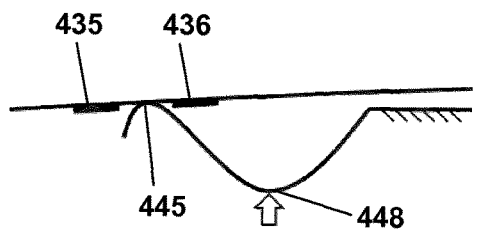

FIG. 6B shows the switch arrangement in an intermediate state in which the strip contact portion 448 has been moved upwards whereby the second switch has been opened.

Figure 6C:
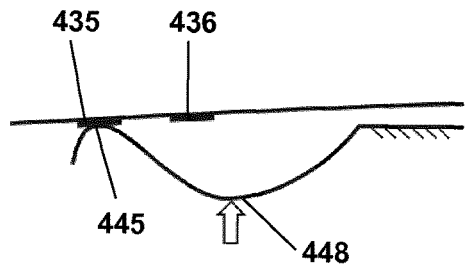

FIG. 6C shows the switch arrangement in a second state in which the strip contact portion 21 has been moved further upwards whereby the first switch has been closed as the strip free end with the common contact point 445 slides into contact with the first stationary switch point 435. When the powered first switch is closed this is detected by the electronic circuitry which subsequently change the state of the first switch from powered to un-powered and the state of the second switch from un-powered to powered.

As appears, a cap-formed add-on device provided with the above-described second switch arrangement can be stored in the first state (cap-off) as well as being mounted on a pen device (cap-on) corresponding to the second state, both states being characterized by having a low power consumption due to a powered open switch. When the add-on cap is mounted on the receiving pen device the switches will change state as follows ("1"=open, "0"=closed):

|  | Switch 1 | Switch 2 |
| --- | --- | --- |
| 1$^{st}$ state | 1 | 0 |
| Interm. state | 1 | 1 |
| 2$^{nd}$ state | 0 | 1 |

The above switch pattern can then be detected as a "cap-on" event (i.e. the cap is put on).

Figure 6D:
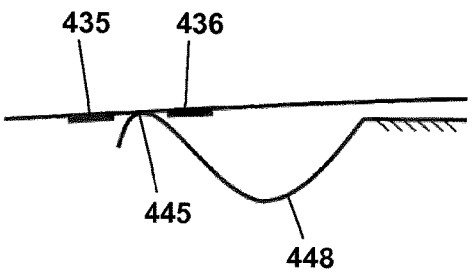

FIG. 6D shows the switch arrangement back in the intermediate state as the strip contact portion 448 has been moved downwards whereby the first switch has been opened but is still un-powered.

Figure 6E:
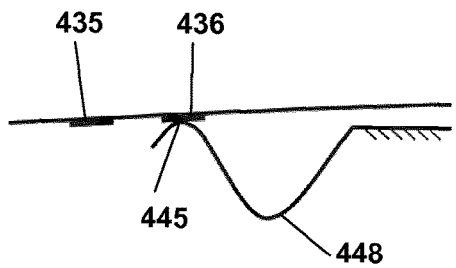

FIG. 6E shows the switch arrangement back in the first state in which the strip contact portion 448 has been moved further downwards whereby the powered second switch has been closed as the strip free end with the common contact point 445 slides into contact with the second stationary switch point 436. When the powered second switch is closed this is detected by the electronic circuitry which subsequently change the state of the first switch from unpowered to powered and the state of the second switch from powered to un-powered.

As appears, when the cap-formed add-on device is removed from the pen device it will return to the low-power cap-off state corresponding to the first state. When the add-on cap is removed from the receiving pen device the switches will change state as follows:

|  | Switch 1 | Switch 2 |
| --- | --- | --- |
| 2$^{nd}$ state | 0 | 1 |
| Interm. state | 1 | 1 |
| 1$^{st}$ state | 1 | 0 |

The above switch pattern can then be detected as a "cap-off" event (i.e. the cap is taken off).

With reference to FIGS. 7A-7E a third embodiment of a switch arrangement 500 will be described, the figures showing a schematic representation of the switch arrangement in different operational states. The switch arrangement comprises a stationary portion 530 (e.g. a PCB) and a moving portion 540. The moving portion is in the form of a strip-formed flexible metal member held in place relative to the stationary part by a holding structure 510 formed by a stationary part. The strip member comprises a contact portion 548 adapted to engage a given structure to which the switch arrangement is being attached. When the contact portion is moved upwards the free end 547 of the strip member is moved in sliding engagement with the stationary portion. The switch arrangement further comprises electronic circuitry and a power source (not shown).

The switch arrangement comprises a single switch comprising a stationary switch point 535 arranged on the stationary portion and a moving switch point 545 arranged on the moving portion in the vicinity of the free end 547. The switch points are connected to and controlled by the electronic circuitry whereby a voltage difference is established between the pair of contact points and thereby a powered switch is provided, this allowing the electronic circuitry to detect when the constantly powered switch is closed or opened.

Figure 7A:
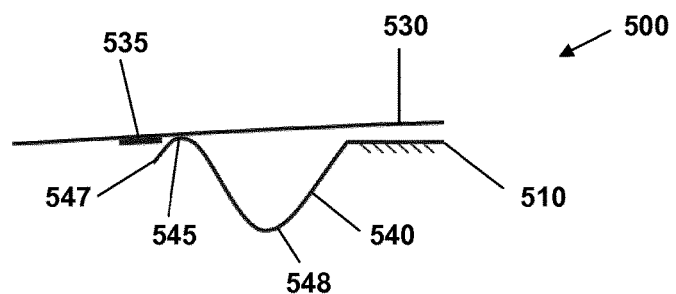
FIGS. 7A-7E show in a schematic representation a third embodiment of a switch arrangement in different operational states.

Turning to FIG. 7A the switch arrangement is shown in a first state in which the powered switch 535, 545 is open.

Figure 7B:
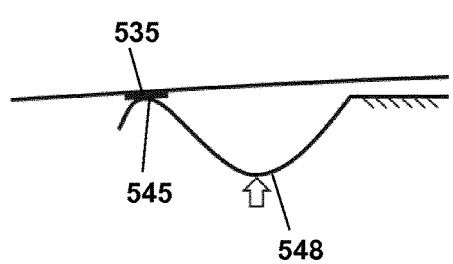

FIG. 7B shows the switch arrangement in an intermediate state in which the strip contact portion 548 has been moved upwards whereby the switch has been closed.

Figure 7C:
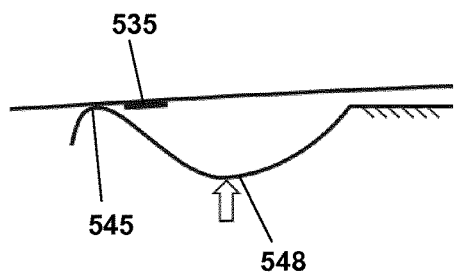

FIG. 7C shows the switch arrangement in a second state in which the strip contact portion 548 has been moved further upwards whereby the switch again has been closed as the strip free end with the contact point 545 slides out of contact with the stationary switch point 535. When the powered switch is closed and subsequently opened this transition is detected by the electronic circuitry, however, in contrast to the above embodiments the single switch remains powered.

As appears, a cap-formed add-on device provided with the above-described third switch arrangement can be stored in the first state (cap-off) as well as being mounted on a pen device (cap-on) corresponding to the second state, both states being characterized by having a low power consumption due to a powered open switch. When the add-on cap is mounted on the receiving pen device the switch will change state as follows ("1"=open, "0"=closed):

|  | Switch |
| --- | --- |
| 1$^{st}$ state | 1 |
| Interm. state | 0 |
| 2$^{nd}$ state | 1 |

The above switch pattern can then be detected as a "cap" event (here: the cap is put on).

Figure 7D:
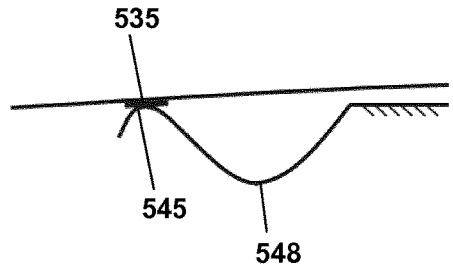

FIG. 7D shows the switch arrangement back in the intermediate state as the strip contact portion 548 has been moved downwards whereby the switch has been closed.

Figure 7E:
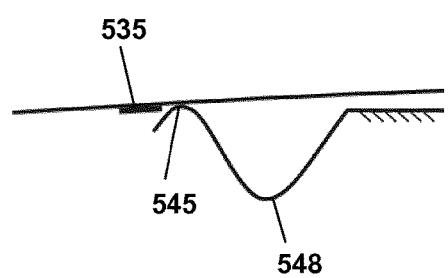

FIG. 7E shows the switch arrangement back in the first state in which the strip contact portion 548 has been moved further downwards whereby the powered switch has been closed as the strip free end with the contact point 545 slides out of contact with the stationary switch point 535. When the powered switch is closed and opened this transition is detected by the electronic circuitry, however, in contrast to the above embodiments the single switch remains powered.

As appears, when the add-on cap is removed from the receiving pen device the switches will change state as follows:

|  | Switch |
|---|---|
| $2^{nd}$ state | 1 |
| Interm. state | 0 |
| $1^{st}$ state | 1 |

The above switch pattern can then be detected as a "cap" event (here: the cap is taken off), however, as the switch patterns for the two events are identical the electronic circuitry cannot distinguish between a cap-on and a cap-off event.

Figure 8:
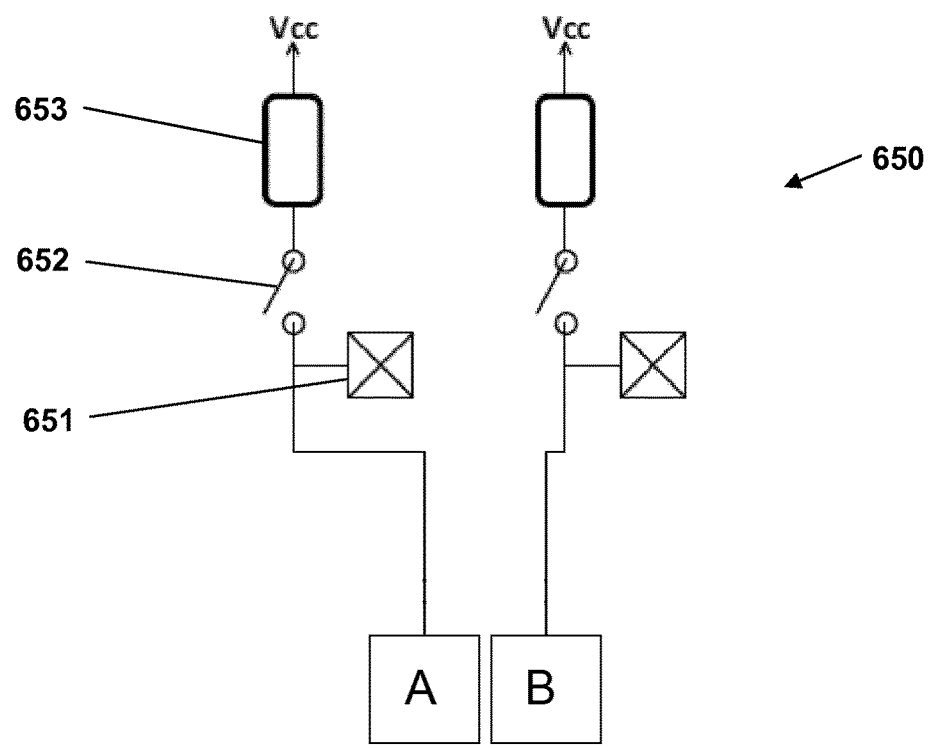
FIG. 8 shows schematically a switch points and microcontroller interface.

FIG. 8 shows schematically in an exemplary embodiment a pair of stationary switch points A and B and a microcontroller (MCU) interface 650, e.g. corresponding to the above-described first and second embodiments 300, 400 each comprising a pair of processor controlled switch points. The two switch points A and B are each connected to switch circuitry comprising an input terminal 551 for a micro controller, a switch 552, a pull-up resistor 553 and a MCU power supply input Vcc. In the shown schematic representation both switch points are un-powered.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. An electronic add-on device adapted to be mounted on a receiving device, comprising:
   electronic circuitry,
   a power source,
   a switch arrangement comprising a first switch and a second switch,
   wherein:
   the switch arrangement has a first state in which:
   the first switch is open and powered, and
   the second switch is closed and un-powered,
   the switch arrangement has an intermediate state in which:
   the first switch is closed and powered, and
   the second switch is closed and powered,
   the switch arrangement has a second state in which:
   the first switch is closed and un-powered, and
   the second switch is open and powered,
   the electronic circuitry is arranged to detect, with the switch arrangement in the first state, when the first switch is closed, and subsequently change the state of the second switch from un-powered to powered, thereby shifting the switch arrangement to the intermediate state, and
   the electronic circuitry is arranged to detect, with the switch arrangement in the intermediate state, when the second switch is opened, and subsequently change the state of the first switch from powered to un-powered, thereby shifting the switch arrangement to the second state.

2. An electronic add-on device as in claim 1, wherein:
   the electronic circuitry is arranged to detect, with the switch arrangement in the second state, when the second switch is closed, and subsequently change the state of the first switch from un-powered to powered, thereby shifting the switch arrangement to the intermediate state, and
   the electronic circuitry is arranged to detect, with the switch arrangement in the intermediate state, when the first switch is opened, and subsequently change the state of the second switch from powered to un-powered, thereby shifting the switch arrangement to the first state.

3. An electronic add-on device as in claim 1, comprising a stationary portion and a moving portion wherein:
   the first switch comprises a first stationary switch point arranged on the stationary portion and a first moving switch point arranged on the moving portion,
   the second switch comprises a second stationary switch point arranged on the stationary portion and a second moving switch point arranged on the moving portion, and
   the moving portion can be actuated from a first state through an intermediate to a second state corresponding to the switch arrangement first, intermediate and second states.

4. An electronic add-on device as in claim 1, wherein the add-on device can be mounted on the receiving device from an off-position through an intermediate position to an on-position corresponding to the switch arrangement first, intermediate and second states.

5. An electronic add-on device as in claim 2, wherein the add-on device can be removed from the receiving device from an on-position through an intermediate position to an off-position corresponding to the switch arrangement second, intermediate and first states.

6. An electronic add-on device adapted to be mounted on a receiving device, comprising:
   electronic circuitry,
   a power source,
   a switch arrangement comprising a first switch and a second switch,
   wherein:
   the switch arrangement has a first state in which:
   the first switch is open and powered, and
   the second switch is closed and un-powered,
   the switch arrangement has a first intermediate state in which:
   the first switch is open and powered, and
   the second switch is open and un-powered,
   the switch arrangement has a second state in which:
   the first switch is closed and un-powered, and
   the second switch is open and powered,
   the electronic circuitry is arranged to detect, with the switch arrangement in the first intermediate state, when the first switch is closed, and subsequently change the state of the first switch from powered to un-powered and the state of the second switch from un-powered to powered, thereby shifting the switch arrangement to the second state.

7. An electronic add-on device as in claim 6, wherein:
   the switch arrangement has a second intermediate state in which:
   the first switch is open and un-powered, and the second switch is open and powered,
the electronic circuitry is arranged to detect, with the switch arrangement in the second intermediate state, when the second switch is closed, and subsequently change the state of the first switch from un-powered to powered and the state of the second switch from powered to un-powered, thereby shifting the switch arrangement to the first state.

8. An electronic add-on device as in claim 6, comprising a stationary portion and a moving portion, wherein:
the first switch comprises a first stationary switch point arranged on the stationary portion and a common moving switch point arranged on the moving portion,
the second switch comprises a second stationary switch point arranged on the stationary portion and the common moving switch point arranged on the moving portion, and
the moving portion can be actuated from a first state through an intermediate to a second state corresponding to the switch arrangement first, intermediate and second states.

9. An electronic add-on device as in claim 6, wherein the add-on device can be mounted on the receiving device from an off-position through an intermediate position to an on-position corresponding to the switch arrangement first, first intermediate and second states.

10. An electronic add-on device as in claim 7, wherein the add-on device can be removed from the receiving device from an on-position through an intermediate position to an off-position corresponding to the switch arrangement second, second intermediate and first states.

11. An electronic add-on device adapted to be mounted on a receiving device, comprising:
electronic circuitry,
a power source,
a stationary portion and a moving portion,
a switch arrangement comprising a powered switch, wherein:
the switch comprises a stationary switch point arranged on the stationary portion and a moving switch point arranged on the moving portion,
the switch arrangement has a first state in which the moving switch point is in a first position and the switch is open,
the switch arrangement has an intermediate state in which the switch points are in contact and the switch thus closed,
the switch arrangement has a second state in which the moving switch point is in a second position and the switch is open, and
the electronic circuitry is arranged to detect a transition event when the switch is closed and subsequently opened.

12. An electronic add-on device as in claim 11, wherein the add-on device can be mounted on the receiving device from an off-position through an intermediate position to an on-position corresponding to the switch arrangement first, intermediate and second states.

13. An electronic add-on device as in claim 11, wherein the add-on device can be removed from the receiving device from an on-position through an intermediate position to an off-position corresponding to the switch arrangement second, intermediate and first states.

14. An electronic add-on device as in claim 1, wherein the electronic circuitry is adapted to create a time-stamp when a powered switch is closed or opened.

15. An assembly comprising an electronic add-on device as in claim 1, in combination with a receiving device, wherein:
the receiving device is in the form of a drug delivery device, and
the electronic add-on device is in the form of a cap adapted to be mounted on the drug delivery device.

* * * * *